(12) United States Patent
Kim

(10) Patent No.: US 9,623,064 B2
(45) Date of Patent: Apr. 18, 2017

(54) FERMENTED FOOD IMPROVING BOWEL FUNCTIONS WITH STERCORAL REMOVAL EFFICIENCY AND MANUFACTURING METHOD THEREOF

(71) Applicant: Goo Whan Kim, Daejeon (KR)

(72) Inventor: Goo Whan Kim, Daejeon (KR)

(73) Assignee: Goo Whan Kim, Daejeon (KR)

( * ) Notice: Subject to any disclaimer, the term of this patent is extended or adjusted under 35 U.S.C. 154(b) by 0 days.

(21) Appl. No.: 14/606,738

(22) Filed: Jan. 27, 2015

(65) Prior Publication Data

US 2016/0089408 A1    Mar. 31, 2016

(30) Foreign Application Priority Data

Sep. 29, 2014  (KR) .................... 10-2014-0130159

(51) Int. Cl.
| | |
|---|---|
| *A61K 36/68* | (2006.01) |
| *A23L 33/105* | (2016.01) |
| *A23L 19/20* | (2016.01) |
| *A61K 36/064* | (2006.01) |
| *A61K 36/232* | (2006.01) |
| *A61K 36/62* | (2006.01) |
| *A61K 35/744* | (2015.01) |

(52) U.S. Cl.
CPC .............. *A61K 36/68* (2013.01); *A23L 19/20* (2016.08); *A23L 33/105* (2016.08); *A61K 36/064* (2013.01); *A61K 36/232* (2013.01); *A61K 36/62* (2013.01); *A23Y 2220/03* (2013.01); *A23Y 2220/13* (2013.01); *A23Y 2220/67* (2013.01); *A61K 35/744* (2013.01)

(58) Field of Classification Search
CPC ............................. A61K 36/21; A23L 1/3002
See application file for complete search history.

(56) References Cited

U.S. PATENT DOCUMENTS

2010/0316763 A1* 12/2010 Choi ...................... A23K 1/007
426/18

FOREIGN PATENT DOCUMENTS

| KR | 20010044542 A1 * | 6/2001 |
|---|---|---|
| KR | 20040018569 A1 * | 3/2004 |
| KR | 1020040018569 | 3/2004 |
| KR | 100429086 | 4/2004 |
| KR | 100506824 | 8/2005 |
| KR | 100512322 | 8/2005 |
| KR | 20070016473 A1 * | 2/2007 |
| KR | 100891608 | 4/2009 |
| KR | 100937455 | 1/2010 |
| KR | 1020130029283 | 3/2013 |
| KR | 2013130201 A1 * | 12/2013 |

OTHER PUBLICATIONS

Office Action issued by the Korean Intellectual Property Office on Feb. 25, 2016.

* cited by examiner

*Primary Examiner* — Louise W Humphrey
*Assistant Examiner* — Stephen A Perkins
(74) *Attorney, Agent, or Firm* — I P & T Group LLP

(57) ABSTRACT

Exemplary embodiments of the present invention provide fermented foods improving bowel functions with stercoral removal efficiency and a manufacturing method thereof. The manufacturing method of the fermented foods improving bowel functions includes a first process in which herb powder and glasswort powder placed in a cloth pouch together are heated in a potable water, and a second process in which the previously heated mixture is fermented at 20-50° C. with fermenting strain. In a third process, the previously fermented mixture may be solidified then kneaded with psyllium husk powder and the fermented liquid.

7 Claims, 3 Drawing Sheets

_FERMENTED FOOD IMPROVING BOWEL FUNCTIONS WITH STERCORAL REMOVAL EFFICIENCY AND MANUFACTURING METHOD THEREOF_

CROSS-REFERENCE TO RELATED APPLICATION

This application claims priority from and the benefit of Korean Patent Application No. 10-2014-0130159, filed on Sep. 29, 2014, which is hereby incorporated by reference in its entirety.

BACKGROUND

Technical Field

Exemplary embodiments of the present invention relate to fermented food improving bowel functions with stercoral removal efficiency.

Discussion of the Background

Constipation is the symptom accompanying possible discomfort during defecation or physiological disorder resulting from abnormally stiff and dry feces or decreased defecation frequency.

Westernized lifestyle and instant food changed the overall dietary lifestyle. Meals mainly with high-protein and low-dietary fiber food, and food made with fine grain particles resulting from development in food powdering are not easily absorbed in bowel that may lead to abuse of digestive organs caused by discomfort with stercoral, pain during defecation.

With these problems in mind, products have been developed focusing on stercoral removal efficiency by increasing defecation, facilitating defecation from shutting out autonomic nerves, or providing ferment bacilli beneficial for the bowel.

Though some products fermented with strains beneficial to the bowel such as Bifidobacteria or _Lactobacillus_ are available, fermented drinks are insufficient in enhancing bowel movement or removing stercoral.

Published Korean Patent 10-0506824 (Natural medicine compound for improvement of bowel function and constipation remedy) describes several natural medicine compounds of which essential components are radish or tea. The aforementioned compounds are manufactured by thermal aqueous extraction with water or aqueous ethanol, followed by powdered extract.

Published Korean Patent Application Publication 10-2013-0029283 (Constipation-remedy compounds) describes compounds to remedy constipation including the extract from one or more of ixeridium, castor, perilla seeds, and sea mustard stem, as an active ingredient.

Published Korean Patent 10-0429086 describes supplementary health food compounds manufactured by mixing senna leaves and machilus thunbergii. Sennoside is not extracted from these ingredients.

The aforementioned techniques are made with powdered ingredients, or extracts prepared by water or aqueous alcohol, which take a long time to treat constipation and may not satisfy customer's needs.

SUMMARY

Exemplary embodiments of the present invention provide a manufacturing method of the fermented food improving bowel functions including a first process in which herb powder and glasswort powder placed in a bag, e.g., a cloth pouch together are heated in a potable water, followed by a second process in which the previously heated mixture is fermented at 20-50° C. with fermenting strain. In a third process, the fermented mixture may be solidified then kneaded with psyllium husk powder and the fermenting liquid. In a fourth process, the kneaded mixture may be shaped into spherical shapes or tablet followed by drying, or the mixture is powdered.

Exemplary embodiments of the present invention may improve constipation, removal of stercoral, and irritable bowel syndrome through facilitating bowel movement. This is done by providing dietary ingredients of psyllium husk with bowel function improving food made of herb.

Exemplary embodiments of the present invention provide a manufacturing method of such bowel function improving food in sphere or tablet forms so that consumers can conveniently intake or store. Additional features of the invention will be set forth in the description which follows, and in part will be apparent from the description, or may be learned by practice of the invention.

Exemplary embodiments of the present invention provide a fermented food for improving bowel function and a manufacturing method thereof. The method may include the following processes using herbs to fulfill the aforementioned purposes:

a first process in which powdered herbs and glasswort are heated in a cloth pouch with potable water;

a second process in which the potable water heated along with herb powder and glasswort powder are fermented with fermenting strain at 20-25° C. to produce a fermented solid compound and fermented liquid;

a third process in which the fermented solid compound is kneaded with psyllium husk powder and the fermented liquid; and a fourth process in which the kneaded mixture is produced into spherical form or tablet followed by drying, or granulization of the mixture.

The herbal powder in the first process may include one or more of the following herbs: nelumbo semen, angelica gigas, aucklandia lappa, betel, senna, immature trifoliae orange, rhubarb, cannabis seeds, peach kernel.

The fermenting strain in the second process may include one or more of the following _Lactobacillus_ or Bifidobacteria: _Bacillus subtilis, Saccharomyces cerevisiae, Lactobacillus acidophilus, Lactobacillus brevis, Lactobacillus plantarum._

The third process may include: first adding psyllium husk powder (30-50 wt % of the fermented solid compounds) then the fermenting liquid to the compound (1-3 wt %).

Exemplary embodiments of the present invention provide the preparation method for fermented food for improving bowel function with which the intrinsic efficacy of dietary fiber from psyllium husk, and the enforcement of beneficial bacteria in bowel through fermentation with fermenting strain can be utilized for constipation remedy and prevention.

Exemplary embodiments of the present invention may also offer convenient consumption for customers since this food with bowel function improvement is provided as a form of sphere of tablets.

DETAILED DESCRIPTION OF THE ILLUSTRATED EMBODIMENTS

Figure 1:
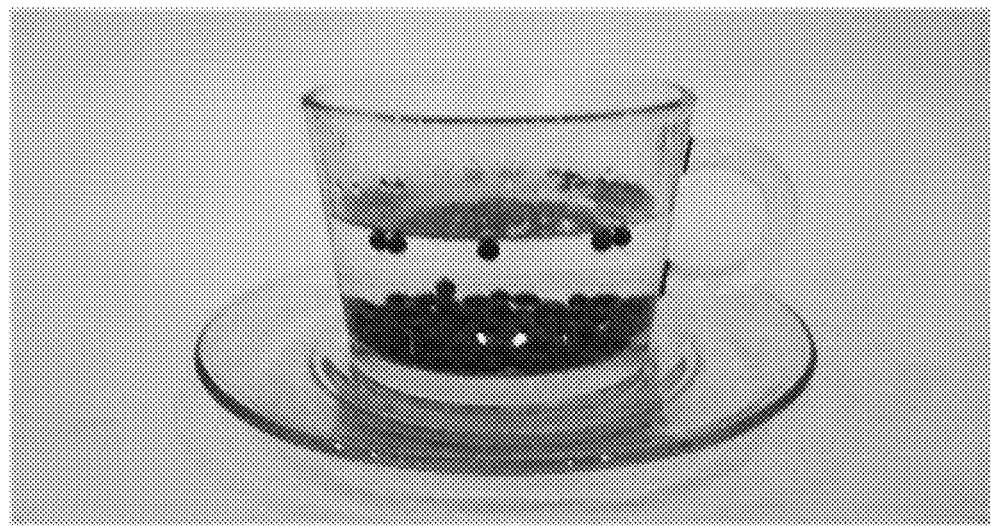
FIG. 1 illustrates fermented food for improving bowel function in potable water prepared according to an exemplary embodiment of the present invention.
Figure 2:
FIG. 2 illustrates fermented food for improving bowel function in potable water 24 hours after it is prepared according to an exemplary embodiment of the present invention.
Figure 3:
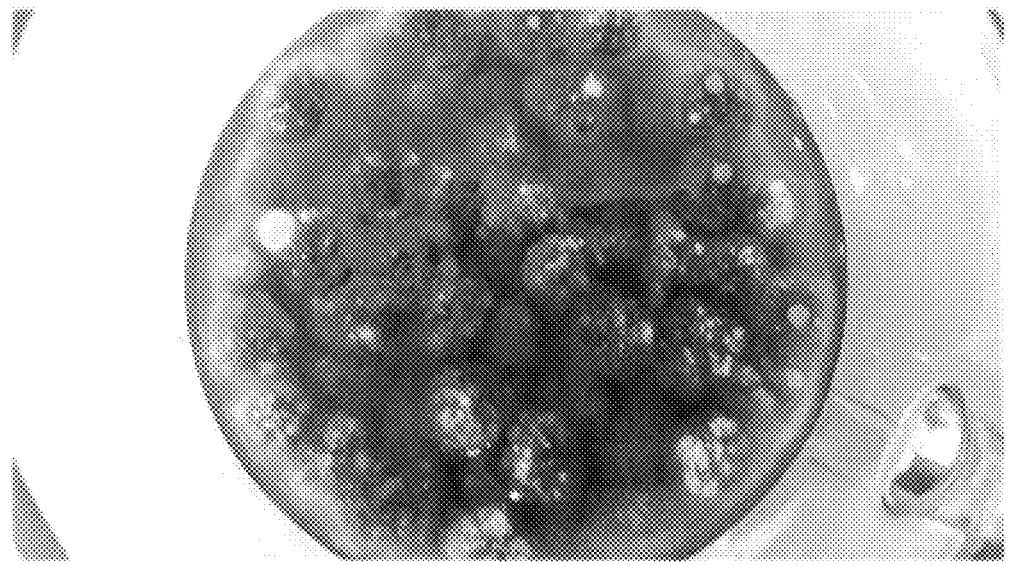
FIG. 3 illustrates cultivated *Lactobacillus* in the fermented food for improving bowel function in potable water three days after it is prepared according to an exemplary embodiment of the present invention.
Figure 4:
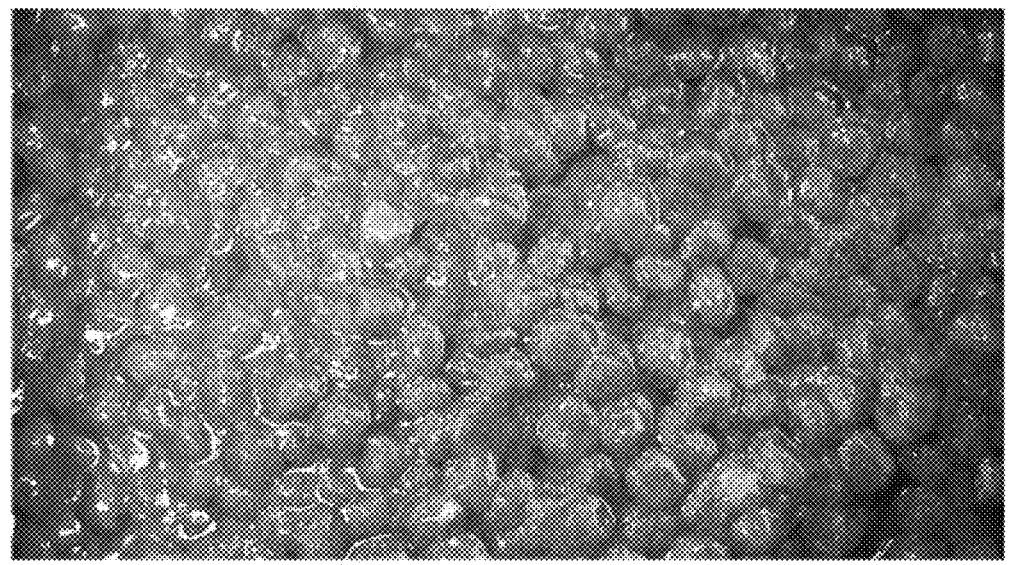
FIG. 4 illustrates fermented food for improving bowel function absorbed with water prepared according to an exemplary embodiment of the present invention.
Figure 5:
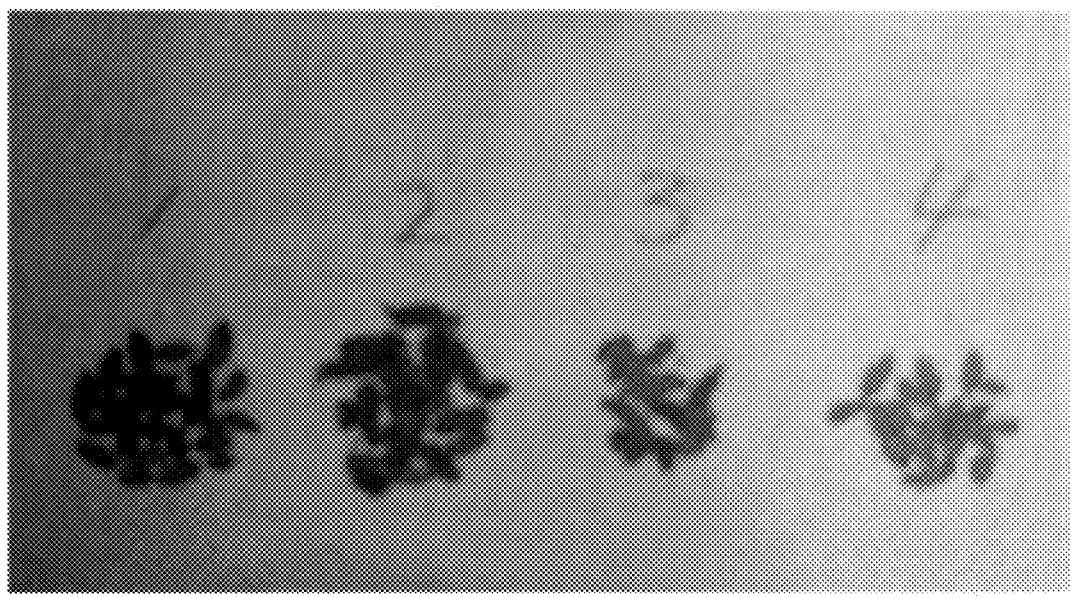
FIG. 5 illustrates the feces of mice. Under 1 and 2 are the feces from the mice fed with glasswort, the main ingredient of salicornia herbacea or saltwort, and under 3 and 4 are the feces from the mice with common feed.

Exemplary embodiments of the present invention provide fermented food for improving bowel function with stercoral removal efficacy and the preparation method.

The ways to facilitating defecation may include; various ways of coating psyllium husk as dietary fiber supplement for stercoral removal or weight loss; herb for constipation remedy using herbs such as angelica gigas; aurantii immaturus fructus; polygoni multiflori radix, the constipation remedy by activating microbes in bowel using ferment bacilli; a way to enhance bowel health with aloe mixed with psyllium husk and other natural ingredient; a constipation remedy using sea plants such as sea tangle or sea laver; a way to use glasswort powder or glasswort extract to prepare a drink for constipation remedy and bowel function improvement; a way to remedy constipation with extract from fermented rice bran or leaven extract, a way to remedy constipation and improve bowel function using different raw materials depending on individual constitution; a way to resolve constipation with horse placenta as a main ingredient; a way to manufacture fermented food with complex fermenting steps with powdered ingredients; a way to increase bowel movement by increasing beneficial bacterial in bowel, and the like. In addition, adrenergic inhibitors, manipulation such as enema, and bowel evacuant can be used. However, these methods may, in long run, cause bowel lethargy and constipation may persist. Though many attempts with the above mentioned methods increase bowel movement or remedy constipation are partly successful, it lacks overall effectiveness, biological stability, and economic efficacy.

According to the preferred exemplary embodiments of the present invention, the manufacturing method of the aforementioned fermented foods which improve bowel functions includes: a first process in which herbal powder and glasswort powder placed in a cloth pouch together are heated in a potable water, followed by a second process in which the heated mixture is fermented at 20-50° C. with fermenting strain. The method may further include a third process in which the fermented mixture is solidified then kneaded with psyllium husk powder and a fermenting liquid, followed by a fourth process in which the kneaded mixture is shaped into spherical shapes or tablet followed by drying, or the mixture is powdered.

The herbal powder in the first process may include one or more of the following herbs: nelumbo semen, angelica gigas, aucklandia lappa, betel, senna, immature trifoliae orange, rhubarb, cannabis seeds, peach kernel.

The fermenting strain in the second process may include one or more of the following *Lactobacillus* or Bifidobacteria: *Bacillus subtilis, Saccaromyces cerevisiae, Lactobacillus acidophilus, Lactobacillus brevis, Lactobacillus plantarum*. The fermenting temperature is either at room temperature or 20-50° C., or the temperature close to that of bowel interior. It may be preferable to set the temperature range of 35-45° C. but, more preferably, 38-42° C.

The third process may include: first adding psyllium husk powder (30-50 wt % of the fermented solid compounds) then the fermenting liquid to the compound (1-3 wt %).

The aforementioned fermented food for improving bowel function manufactured with the previously described process is recommended for fermented food for improving bowel function.

The use of herbs with efficacy to bowel functions may be preferable, and these herbs may include glasswort, nelumbo semen, angelica gigas, aucklandia lappa, betel, senna, immature trifoliae orange, rhubarb, cannabis seeds, and peach kernel. However, aspects of the present invention are not limited as such.

Glasswort is one kind of salicornia herbacea under chenopodiaceae family of caryophyllales order. It grows about 10-30 cm high with branches that grow symmetrically. The perianths are fleshy and tubby with one or two stamen and two styles. Its fruits are utricles covered with perianths having black seeds. This is an herbal annual forming colonies near mudflats where sea water comes in and out or inland with high salt concentration. It thrives well in a crude environment with high salt concentration. The leaves sprout around May and June, then turn dark green around July and August in Korea. In October, it turns red with fruition of flat and round fruit. Glasswort grows in mudflats with high mineral and salt content, characterized by high water content above 90% and salty taste. Glasswort has minerals and inorganics such as iron, calcium, potassium, magnesium, phosphorus, and other. These trace elements are beneficial to human bodies and necessary for life activities.

Nelumbo semen is the well-matured fruits and seeds of nelumbo nucifera gaertner. It is used to treat hemorrhoids, anal prolapse, bleeding in uterus, severe itchiness, neurasthenia, and anxiety. It contains starch, raffinose, protein, fat, carbohydrate, potassium and the like.

Angelica gigas has efficacy of blood production, therefore widely used to treat diseases related to blood. Angelica gigas nakai, angelica sinensis, angelica acutiloba kitagawa are used. Angelica gigas increase blood flow in coronary artery, and promotes red blood cell production. An ancient agricultural literature widely used in Asia describes it has sweet and warm trait with no poison. It also records, it warms body, stops pains, cures arthritis, is used when miscarriage of women is likely or for severe itchiness, protects five major organs, produces ligaments and muscles. Compendium of Materia Medica (Bencao Gangmu) states angelica gigas controls blood and is good for female. It treats disease related with chi, palsy, fatigue. It also eliminates bad blood and produces fresh blood. It is good for habitual constipation, and used widely for menstruation and postpartum symptoms. It is also asserted that angelica gigas retards the differentiation of osteoclasts. Decursinol ingredient relieves pain, decursin ingredient has anti-cancer efficacy, and angelan ingredient is good for diabetes. It also promotes red blood cell production and protein synthesis. It works as anti-inflammatory and pain-relieving agent.

Angelica gigas nakai is more efficient in constipation remedy than angelica sinensis or angelica acutiloba kitagawa.

Psyllium husk is seed bark of plantago asistica linne under plantaginaceae family. It reaches large intestines without being resolved even by enzymes. During this process, it decreases internal pressure by absorbing water inside of intestines, delays nutrients such as sugar by affecting the passing time through intestines which beneficially affects the patients with diabetes and obesity. It decreases cholesterol index by being combined with bile acid, provide nutrients to mucous membrane in intestines, and affect microorganisms in intestines. Psyllium husk and bacteria not digested increase the volume of feces by absorbing water. It resolves constipation by affecting the frequency of defecation and weight of feces. It helps easy defecation by removing stercoral.

Aucklandia lappa refers to roots of aucklandia lappa Decne. Aucklandia lappa also smells similar to honey. In one individual it has five roots, five branches for one stem, five leaves for one branch, and five gnarls between leaves. It is said the burnt smell reaches far. Aucklandia lappa is used for pains due to full stomach, flatulent symptoms, vomiting, and diarrhea. It is used to treat chronic inflammation in the digestive systems by facilitating the emission of chi, stomachache, dysentery and orchitis due to its sterile function. Pharmacologically, it undoes convulsion of bronchia and the small intestine, lowers blood pressure, and has antibacterial trait.

Betel is a monocot tree under arecaceae family of arecales order originated from Malaysia. It grows over 25 m and the branch does not divide. The leaves are compound pinnated and 1-2 m long, of which bottom is sheathed and covers the leaf stems. The end of the leaves are cleaved into gear shapes with short footstalk. It is a hermaphrodite with unisexual white flower in spadix forms. The fruit is yellow, orange, or red in color and is in round or long oval shapes with 3 cm-in-radius. The fruit is called betel nut, and over four hundred million people chew these fruit while India consumes one hundred thousand ton. Betel has tannins and alkaloids, and is used to cestode termination, diarrhea, skin disease, headache, and the like. The immature leaves are edible. The fruit is frequently used as dye.

Senna is a subshrub that grows about 1 m with the pinnated leaves in long oval shapes about 4-12 cm long of which edges are flat. The flowers are yellow forming in racemose corymb shape. The fruit is legume, green in summer and brown when dried. Leaves and fruits are used for different purposes, and alexandrian senna and tanner's cassia are the most efficient jollops because of their sennoside content. All anthraquinones stimulate intestinal membranes and induce defecation. The leaves and legumes cleanse and stimulate the lower digestive system, thus used for fasting and eliminating parasites.

Aurantii immaturus fructus is a fruit of poncitus trifoliate halved and dried. These ingredients originated from Korea or somewhere else do not show significant difference in appearance. However, the dried products from Korea have brighter outside color, and flesh inside the rind is thinner for Korean products. The cut surface of the Korean products is yellowish white while the colors of those from other countries are thicker. Among the fruits harvested right after fruition, the smallest is considered high quality. This ingredient also facilitates the flow of chi, the emission of chi from its source, and eliminates phlegm accumulation.

Rhubarb is an oriental medicinal herb made with the roots of herbaceous perennial rheum rhabarbarum in the family polygonaceae. The roots of long-leaved rhubarb, Tang-dynasty rhubarb, and medicinal rhubarb are used. In Korea, rhubarb roots of Chinese origin are used since they are not autogenous in Korea. Rumex longifolius or rumex aquaticus that are known to grow in the Korean peninsula are used instead, but also known to have lower efficacy. The outside of the medicine is yellowish or light brown with white and fine reticulation formed in a very tight and strong manner. Inner tissues are in an annulus shape forming from small and brown circles, or in irregular shapes. Rhubarb is yellow and has fast medicinal effect. It is also called "a general" because its medicinal character which promotes excretion of aged materials and provide new ingredient is similar to that of a general who defeats enemies and establishes peace and prosperity. It has peculiar smell, and feels like fine sands when put into a mouth. It has astringent and bitter taste with cold trait. Rhubarb induces bowel excavation which eliminate poison and fever. It cleanses the stomach and intestines, promotes metabolism, and treats constipation with fever and stuffed stomach. It works on headache, blood congestion, throat pain, constipation, nose bleeding, blood spitting, abscess, and used for edema and diuresis. Pharmacologically, it promotes colon movement, works as antipyretic, lowers body temperature, helps excrete bile, shortens blood clotting time, sterilizes, promotes diuresis, and protects liver functions.

Cannabis seeds is from cannabis sativa seeds which ameliorates aridness, helps soft bowel movement, and eases blood circulation. It grows straight reaching 2-3 m. The flower is light green blooming around July and August. It has five flower cups and stamens with yellow anther. The female flow is sheathed with one small lodicule, two styles and one ovary. Its fruits are flat egg shapes. It is grown widely in Korea. It is harvested when fruits are mature in fall and winter followed by drying.

Peach kernel is made with the seeds of peach trees or prunus davidiana. It has little scent, is like oil, tastes bitter and sweet, and its traits are not biased. Since it removes agglomerated dead blood, peach kernel is used for abdomen pain, menstruation obstruction, dysmenorrhea, bruises, lung abscess, and appendicitis. Since it facilitates intestines movement, it is used for constipation as well as skin itchiness, dryness, freckles, and the like. Pharmacologically, it is reported to expand blood vessel, increase blood flow, contract uterus, promote blood clotting in uterus, help defecation, suppress inflammation, dissolve phlegm, relieve pain, fight against allergy, and fight against tumor. The seeds are in unbalanced circle with bilateral asymmetry. One end is pointy while the other is round with chalaza located. The seedcoat is redish or light brown with outer skin looking as though sprinkled with powder due to epidermal cells comprised of stone cells. Fibrovascular structures are distributed on the seedcoat from the chalaza, at which vertical dents are formed. When softened by heating, the seedcoat and transparent white endosperm comes out easily from cotyledon.

The use of bacteria beneficial for bowel is recommended as fermenting strains in the second process mentioned above. These bacteria may be, but not limited to, one or more of the following *Lactobacillus* or *Bifidobacteria: Bacillus subtilis, Saccaromyces cerevisiae, Lactobacillus acidophilus, Lactobacillus brevis, Lactobacillus plantarum.*

*Lactobacillus* is also called lactic acid bacteria, which prevents the growth of pathogen and harmful cells through lactic acid forming through lactic acid fermentation. It may be an important ingredient because it also prevents abnormal fermentation of other bacteria in bowel, and used as a digestive supplement. It is gram-positive, anaerobic or facultative anaerobic with no motility, and mostly catalase-negative. The Lactobacilluses used herein may suppress the growth of harmful bacteria, prevent cardiovascular disease by producing the material controlling immunocompetence, suppress pathogens with sterilization, improve constipation, and prevent diarrhea, gastric ulcer, colon cancer.

Bifidobacteria activates the immune system and peristalsis of intestines by lowering pH inside of bowel. This bacteria is closely related to human health, known to decrease when stressed or sick.

1. The First Process

The first process heats potable water in which powdered herbs and glasswort are placed in a cloth pouch.

The herbal powder may include at least one of nelumbo semen, angelica gigas, aucklandia lappa, betel, senna, immature trifoliae orange, rhubarb, cannabis seeds, and peach kernel. The use of two or more of nelumbo semen, angelica gigas, aucklandia lappa, betel, senna, immature trifoliae orange, rhubarb, cannabis seeds, and peach kernel is preferred.

It is preferred that the glasswort or herbs is powdered with their diameter at 0.01-0.1 mm. It is highly recommended to be at 0.01-0.07 mm, but more preferable diameter is 0.01-0.05 mm.

The herbs powder, glasswort powder, and potable water may be mixed at the weight ratio of (0.7-1.5):(1.5-3):(3-9), respectively, followed by sterilization with heating. More preferably, the ratio is 1:2:(5-8). The heating temperature for sterilization may be 100-125 OC for 10-30 minutes, and a preferred condition is 121° C. for 15 minutes.

2. The Second Process

The second process is a fermenting process in which the potable water heated along with herbal powder and glasswort powder are fermented with fermenting strain at 20-50° C., The injection of fermenting strains is recommended when the temperature of the potable water with herb powder and glasswort powder is at 30-40° C.

The weight ratio of the herb powder, glasswort power, and the fermenting strains may be (0.7~1.5): (1.5~3): (0.01~0.05). It is preferable to keep 1:2: (0.01~0.05) ratio. The fermenting strains may include one or more of *Bacillus subtilis, Saccaromyces cerevisiae, Lactobacillus acidophilus, Lactobacillus brevis*, and *Lactobacillus plantarum*.

The fermentation may be performed at 20-50° C. for 2-7 days. More preferably, the fermentation may be performed with the temperature at 32-38° C. for 3-5 days. The temperature and the duration may be shortened or prolonged depending on ambient temperature. The fermenting temperature at room temperature or below 35° C. leaves sour taste that may be disfavored by customers, and that the fermenting temperature above 45° C. does not effectively cultivate strain.

Further, it is preferred that the fermentation is kept at around 40° C. which is near the temperature of human intestines to ensure fermenting bacteria can be active.

The above strains may be *Lactobacillus* and Bifidobacteria including one or more of *Bacillus subtilis, Saccaromyces cerevisiae, Lactobacillus acidophilus, Lactobacillus brevis*, and *Lactobacillus plantarum*. One or more of the bacteria can be mixed, but the use of all of the above elements is more preferable.

3. The Third Process

The third process is the step of kneading the fermented solid prepared in the second process with psyllium husk powder and the fermented liquid produced from the second process.

After the fermented solid from the second process are separated from the liquid into separate containers, it is recommended the solid still absorbed with the fermented liquid is kneaded with psyllium husk powder with its amount continuously increasing for homogeneous mixing. The diameter of the aforementioned psyllium husk powder is recommended at 0.01-0.1 mm in fine powder form. 0.01-0.07 mm is highly recommended while 0.01-0.05 mm is recommended for a better result.

The mixing ratio of the fermented solid and psyllium husk powder is recommended at (0.7-1.5): (1.5-3) by weight. (1-1.2): (1.7-2.5) is highly recommended, but 1:2 ratio is more preferable. In this case, the mixing weight ratio of the kneaded psyllium husk powder and the fermented liquid is about (1-1.2): (0.1-0.9), but 1: (0.1-0.5) is more preferable.

In the above mentioned kneading, the fermented liquid extracted in the second process is recommended to increase stepwise considering high water content of psyllium husk. The mixing of aforementioned fermented solid, psyllium husk powder, and the fermented liquid is recommended at 1: (0.3-0.5): (0.01-0.03) respectively added in the written order.

In an example, 3 kg of psyllium husk powder may be added to 3.4 kg of the fermented solid and kneaded while additional psyllium husk powder is added to the mixture with 300-500 g increment until the total weight of psyllium husk powder becomes 6 kg. When moisture is needed for kneading, the fermented liquid mentioned above is added 30-90 ml at a time.

Applying pressure during the kneading mentioned above may require no additional binding ingredients in obtaining material properties for preparing spherical pills. It is desired that the kneaded dough is moist and somewhat wet and dry.

Further, adding the solid fermented with the psyllium husk is recommended for convenient consumption of intrinsic dietary ingredient of psyllium husk. Longer time for the spherical pill to unravel while reaching intestines than powdered or coated products is recommended for better water containment.

4. The Fourth Process

During the fourth process, the kneaded mixture from the third process is produced into spherical pills or tablet, followed by drying and powdering in a sphere-shaping machine.

The recommended sphere size is no more than 5 mm in diameter, but around 2.5 mm is more preferable because smaller size is better as long as the psyllium husk is not attached in the mouth. If the diameter is less than 2 mm, the psyllium husk is more likely to be attached in the mouth.

The recommended interior temperature of the drier for the aforementioned spherical pills is 30-80° C. More preferably, the temperature may be set not to exceed 70° C. Since it is from the natural produce, the product may contain benzopyrene when the process is done above 75° C. Therefore, temperature lower than 75° C. is desired. Due to the characteristic of fermented foods, the best methods for drying is freeze drying or low-temperature depressurization. The fermented food can be prepared into spherical pills, tablet, or powder.

Exemplary embodiments of the present invention provide a preparation method of fermented food for improving bowel function and will be described with experimental examples. These examples and embodiments are for illustration purpose only, not to limit the scope of the invention.

Embodiment 1

2.6 kg of glasswort powder, 1.2 kg of nelumbo semen powder, and 12 L potable water are placed inside of a fermenter, followed by sterilization with boiling for two hours. 60 g of fermenting strain including *Bacillus subtilis, Saccaromyces cerevisiae, Lactobacillus acidophilus, Lactobacillus brevis*, and *Lactobacillus plantarum* are injected and kept at 38-42° C. for five days, after which this fermented powder is kneaded with 6 kg psyllium husk powder. 8 kg of bowel-function-enhancing and constipation-remedying food is obtained after drying the mixture prepared in 5-mm-in-diameter spherical shapes.

Embodiment 2

2.6 kg of glasswort powder, 600 g of angelica gigas powder, 600 g of peach kernel and 12 L potable water are placed inside of a fermenter, followed by sterilization with boiling for two hours. 60 g of fermenting strain including *Bacillus subtilis, Saccaromyces cerevisiae, Lactobacillus acidophilus, Lactobacillus brevis*, and *Lactobacillus plantarum* are injected and kept at 38-42° C. for five days, after which this fermented powder is kneaded with 6 kg psyllium husk powder. 8 kg of bowel-function-enhancing and constipation-remedying food is obtained after drying the mixture prepared in 5-mm-in-diameter spherical shapes.

Embodiment 3

2.6 kg of glasswort powder, 1.2 kg of nelumbo semen powder, and 12 L potable water are placed inside of a fermenter, followed by sterilization with boiling for two hours. 60 g of fermenting strain including *Bacillus subtilis, Saccaromyces cerevisiae, Lactobacillus acidophilus, Lactobacillus brevis*, and *Lactobacillus plantarum* are injected and kept at 38-42° C. for three days, after which this fermented powder is kneaded with 5 kg psyllium husk powder and 1 kg of peach seed powder. 8 kg of bowel-function-enhancing and constipation-remedying food is obtained after drying the mixture prepared in 5-mm-in-diameter spherical shapes.

Embodiment 4

2.6 kg of glasswort powder, 1.2 kg of nelumbo semen powder, and 12 L potable water are placed inside of a fermenter along with a hemp pouch including each of angelica gigas, aucklandia lappa, betel, senna, immature trifoliae orange, rhubarb, cannabis seeds, and peach kernel (60 g each; 480 g total in the hemp pouch). It is followed by sterilization with boiling for two hours, after which the hemp pouch with angelica gigas, aucklandia lappa, betel, senna, immature trifoliae orange, rhubarb, cannabis seeds, and peach kernel, is removed. After the temperature is reduced to 33-37° C., 60 g of fermenting strain including *Bacillus subtilis, Saccaromyces cerevisiae, Lactobacillus acidophilus, Lactobacillus brevis*, and *Lactobacillus plantarum* are injected and kept at 38-42° C. for three days, after which this fermented powder is kneaded with 6 kg psyllium husk powder. 8 kg of bowel-function-enhancing and constipation-remedying food is obtained after drying the mixture prepared in 5-mm-in-diameter spherical shapes.

Experiment 1

The levels of satisfaction (satisfaction) from female subjects with constipation were investigated after they consume the bowel function improving food prepared in the above mentioned Embodiments 1, 2, 3, and 4. The items investigated were satisfaction regarding constipation, feeling of remaining feces after defecation (remaining feces), feeling at abdomen (abdomen feeling), weight loss, filled-stomach feeling, amount of meal consumption (meal amount), headache, frequency of defecation (frequency), desire for defecation (desire), constipation during menstruation, and skin. The words in parentheses are used in Table 1 where applicable.

TABLE 1

| Items | | Comments | Satisfaction |
| --- | --- | --- | --- |
| 1 | constipation | no constipation after 1-2 days of consumption. | Very High |
| 2 | remaining feces | no feeling of remaining feces, no use of videt | Very High |
| 3 | abdomen feeling | empty and cleared feeling | High |
| 4 | weight loss | change in waist size | Middle |
| 5 | filled-stomach feeling | hungry | Middle |
| 6 | meal amount | no change in consumption | Middle |
| 7 | headache | no migrane prevalent during constipation | High |
| 8 | frequency | normally once-in-2-3 days defecation with pain before using the fermented food/easy defecation everyday after use of the fermented food. | Very High |
| 9 | desire | difficult bowel movement before using the fermented food despite large vegetable consumption/easy bowel movement everyday after using the fermented food | High |
| 10 | constipation during menstruation | headache, frozen shoulder pain came with severe constipation is gone | Very High |
| 11 | skin | clear, smooth skin with no rash | High |
| 12 | desire | missed bowel movement timing, resolved constipation due to small meals | High |

Table 1 shows all tested individuals showed high level of satisfaction. It also confirms significant efficiency in remedying constipation for the working female subjects during menstruation.

The efficacy of the spherical pills becomes prevalent after one or two days of consumption, imposing little problem to human body.

It will be apparent to those of ordinary skill in the art that various modifications can be made to the exemplary embodiments of the invention described above. However, as long as modifications fall within the scope of the appended claims and their equivalents, they should not be misconstrued as a departure from the scope of the invention itself.

What is claimed is:

1. A method for manufacturing a fermented food for improving bowel function, the method comprising:
heating a pouch of herb powder and glasswort powder in a potable water;
fermenting the heated mixture at 20-50° C. with a fermenting strain to produce a fermented solid compound and fermented liquid;
separating the fermented solid compound from the fermented liquid; and
kneading the fermented solid compound with psyllium husk powder and a first portion of the fermented liquid at a weight ratio of 1:(0.3~0.5):(0.01~0.03) to produce a first kneaded compound; and
kneading the first kneaded compound with additional psyllium husk powder and a second portion of the fermented liquid, wherein a weight ratio of the fermented solid compound in the first kneaded compound: the additional psyllium husk powder: the second portion of the fermented liquid is set at 1:(0.3~0.5):(0.01~0.03) to produce a second kneaded compound.

2. The method of claim 1, further comprising: shaping the kneaded mixture produced from the second kneaded compound into one or more spherical shapes or tablets.

3. The method of claim 1, wherein the fermenting strain comprises: one or more of *Bacillus subtilis, Saccharomyces cerevisiae, Lactobacillus acidophilus, Lactobacillus brevis*, and *Lactobacillus plantarum*.

4. The method of claim 1, further comprising repeated kneading processes, wherein the fermented solid compound remains at a constant weight within a processed kneaded compound and wherein a weight ratio of the fermented solid compound: added psyllium husk powder and added portion of the fermented liquid is set at 1:(0.3~0.5):(0.01~0.03) within the repeated kneading processes until a weight ratio of the fermented solid compound and total psyllium husk powder reaches (0.7-1.5):(1.5-3).

5. The method of claim 1, wherein the herb powder comprises one or more of nelumbo semen, angelica gigas, aucklandia lappa, betel, senna, immature trifoliae orange, rhubarb, cannabis seeds, and peach kernel.

6. The method of claim 1, wherein the herb powder comprises nelumbo semen, angelica gigas, aucklandia lappa, betel, senna, immature trifoliae orange, rhubarb, cannabis seeds, and peach kernel.

7. The method of claim 1, wherein the fermenting strain comprises: *Bacillus subtilis, Saccharomyces cerevisiae, Lactobacillus acidophilus, Lactobacillus brevis*, and *Lactobacillus plantarum*.

\* \* \* \* \*